United States Patent
Kadam et al.

(10) Patent No.: US 8,846,982 B2
(45) Date of Patent: Sep. 30, 2014

(54) PROCESS FOR THE PREPARATION OF HYDROQUINONES

(75) Inventors: Shahuraj Hanamantrao Kadam, Maharashtra (IN); Shashikumar Paknikar, Goa (IN)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/639,448

(22) PCT Filed: Mar. 17, 2011

(86) PCT No.: PCT/EP2011/001316
§ 371 (c)(1),
(2), (4) Date: Nov. 8, 2012

(87) PCT Pub. No.: WO2011/128018
PCT Pub. Date: Oct. 20, 2011

(65) Prior Publication Data
US 2013/0211149 A1    Aug. 15, 2013

(30) Foreign Application Priority Data
Apr. 15, 2010 (EP) .................... 10003959

(51) Int. Cl.
| | |
|---|---|
| C07C 47/565 | (2006.01) |
| C07C 45/69 | (2006.01) |
| C07C 37/01 | (2006.01) |
| C07C 37/56 | (2006.01) |

(52) U.S. Cl.
CPC ............. C07C 37/01 (2013.01); C07C 47/565 (2013.01); C07C 37/56 (2013.01); C07C 45/69 (2013.01)
USPC .......................................... 568/763; 568/436

(58) Field of Classification Search
CPC ...... C07C 47/565; C07C 37/56; C07C 45/69; C07C 37/01
USPC .......................... 568/765, 763, 436
See application file for complete search history.

(56) References Cited

U.S. PATENT DOCUMENTS

| | | | | |
|---|---|---|---|---|
| 3,833,660 | A * | 9/1974 | Smith ............................ | 568/436 |
| 5,364,983 | A * | 11/1994 | Weisse et al. .................. | 568/771 |
| 2006/0128745 | A1* | 6/2006 | Lackey et al. ................. | 514/300 |
| 2010/0267992 | A1* | 10/2010 | Rinker et al. .................. | 568/315 |

FOREIGN PATENT DOCUMENTS

| | | | | |
|---|---|---|---|---|
| WO | 2008/149379 | * | 12/2008 | ........... C07D 231/14 |
| WO | 2009/109872 | * | 9/2009 | ........... C07D 413/04 |

OTHER PUBLICATIONS

Matsumoto et al., Acid-Catalyzed Oxidation of Benzaldehyde to Phenols by Hydrogen Peroxide, Journal of Organic Chemistry, 49, 4740-4741 (1984).*
Jeong, Tae-Sook, et al., Novel 3,5-diaryl pyrazolines as human acyl-CoA:cholesterol acyltransferase inhibitors, Bioorganic & Medicinal Chemistry Letters, 2004, pp. 2715-2717, vol. 14, No. 11.
Matsumoto, Masakatsu, et al., Acid-Catalyzed Oxidation of Benzaldehydes to Phenols by Hydrogen Peroxide, J. Org. Chem., 1984, pp. 4740-4740, vol. 49, No. 24.
Singh, I.P., Synthesis of some aromatic aldehydes and phenols as potential male antifertility agents, Indian Journal of Chemistry, 1989, pp. 692-694, vol. 28B.
Smith, William E., Formylation of Aromatic Compounds with Hexamethylenetetramine and Trifluoroacetic Acid, The Journal of Organic Chemistry, 1972, pp. 3972-3973, vol. 37, No. 24.

* cited by examiner

Primary Examiner — Paul A Zucker
Assistant Examiner — Mark Luderer
(74) Attorney, Agent, or Firm — EMD Serono Research Institute

(57) ABSTRACT

The invention relates to a process for the preparation of a hydroquinone compound of formula (I)

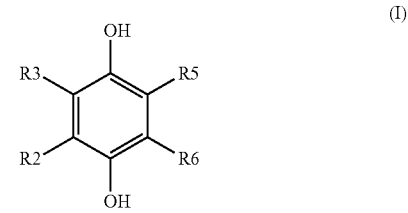

wherein R2, R3, R5 and R6 have the meaning according to claim 1, with the steps of formylating a substituted phenol and oxidizing the resulting substituted 4-hydroxy-benzaldehyde under acidic conditions to the corresponding hydroquinone of formula (I). Another object of the invention concerns the intermediate 2,3,5-trimethyl-4-hydroxy-benzaldehyde for synthesis of 2,3,5-trimethyl-hydroquinone (TMHQ) and (dl) α-tocopherol.

20 Claims, No Drawings

PROCESS FOR THE PREPARATION OF HYDROQUINONES

The invention relates to a process for the preparation of a hydroquinone compound of formula (I)

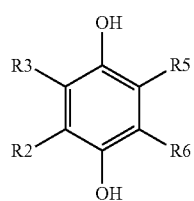

wherein R2, R3, R5 and R6 have the meaning according to claim 1, with the steps of formylating a substituted phenol and oxidising the resulting substituted 4-hydroxy-benzaldehyde under acidic conditions to the corresponding hydroquinone of formula (I). Another object of the invention concerns the intermediate 2,3,5-trimethyl-4-hydroxy-benzaldehyde for synthesis of 2,3,5-trimethyl-hydroquinone (TMHQ) and (dl) α-tocopherol.

Oxidation reactions can produce free radicals, which start chain reactions that damage cells. Antioxidants terminate these chain reactions by removing free radical intermediates, and inhibit other oxidation reactions by being oxidised themselves. Organisms contain a complex network of antioxidant metabolites and enzymes that work together to prevent oxidative damage to cellular components such as DNA, proteins and lipids. As oxidative stress might be an important part of many human diseases, the use of antioxidants in pharmacology is intensively studied, particularly as treatments for stroke and neurodegenerative diseases. Antioxidants are also widely used as ingredients in dietary supplements in the hope of maintaining health and preventing diseases such as cancer and coronary heart disease. In addition to these uses of natural antioxidants in medicine, these compounds have many industrial uses, such as preservatives in food and cosmetics and preventing the degradation of rubber and gasoline. A specific example is 2-tert.-butyl-hydroquinone, which is used as an antioxidant in foods.

It has been claimed that α-tocopherol is the most important lipid-soluble antioxidant, and that it protects cell membranes from oxidation by reacting with lipid radicals produced in the lipid peroxidation chain reaction. 2,3,5-trimethyl-hydroquinone (TMHQ) is a key material for the manufacture of (dl)α-tocopherol and its acetate and other derivatives on an industrial scale. Although numerous processes are described, the state-of-the-art process followed for the past 25 years is still afflicted with several drawbacks. In particular, the production of $MNO_2$ and $MNSO_4$ sludge (acid water) raise an ecological challenge.

Therefore, the technical problem forming the basis of the present invention is to overcome the drawbacks of prior art and to provide an uncomplicated process for the preparation of hydroquinones, especially such a process starting from inexpensive and readily available materials and achieving high yields.

The present invention solves this problem by providing a process for the preparation of a hydroquinone compound of formula (I)

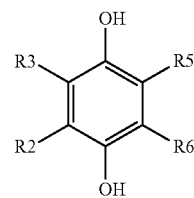

wherein
R2, R3, R5, R6 is independently from one another H, A, Cyc, Hal, CN, —(CYY)$_n$—OA, —(CYY)$_n$—NYY, —O(CYY)$_n$—OA, —O(CYY)$_n$—NYY, —NH(CYY)$_n$—OA or —NH(CYY)$_n$—NYY;
Y is H, A or Hal;
A is unbranched or branched alkyl having 1-10 C atoms, in which 1-7 H atoms can be replaced by Hal, and/or in which one or two adjacent $CH_2$ groups can be replaced independently of one another by a —CH=CH— and/or —C≡C— group;
Cyc is cycloalkyl having 3-7 C atoms, in which 1-4 H atoms can be replaced independently from one another by A, Hal and/or OY;
Hal is F, Cl, Br or I; and
n is 0, 1, 2, 3, 4, 5 or 6;
comprising the steps of:
(a) heating a phenol compound of formula (II)

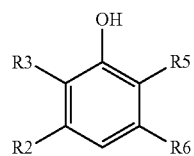

wherein R2, R3, R5 and R6 have the meaning as defined above,
with less than one molar equivalent of a formyl carbon source in an organic acid, followed by adding a hydrolysis medium and heating the resulting mixture to yield a 4-hydroxy-benzaldehyde compound of formula (III)

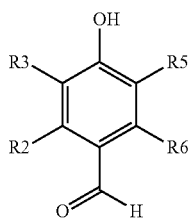

wherein R2, R3, R5 and R6 have the meaning as defined above,
and
(b) reacting the compound of formula (III) with an oxidising agent in a solvent under acidic conditions to yield the compound of formula (I).

It has been surprisingly demonstrated by the inventors that the sequential performance of a Duff reaction and Dakin reaction, each under considerable changes in the reaction conditions and work-up procedure, afforded corresponding hydroquinones of formula (I) in excellent yields. Before filing this application, it has only been known to use hexamethylenetetramine in the Duff reaction to effect formylation of 2,6-disubstituted phenols (Smith JOC 37: 3972-3973 (1972)). It has also been known by EP 0650952 A1 that 3,5-di-tert.-butylsalicylaldehyde can be prepared by heating 2,4-di-tert.-butylphenol and one to three equivalents of hexamethylenetetramine in glacial acetic acid, adding 20% (v/v) sulphuric acid and heating the mixture again. The methods of formylation of 2,6-disubstituted phenols are complicated, give only average yields and employ expensive, eco-critical reagents, such as high amounts of hexamethylenetetramine. Moreover, the Dakin oxidation of 4-hydroxy-benzaldehydes is only reported under alkaline conditions, which are not suitable for hydroquinone synthesis. By the provision of the inventive process, substituted hydroquinones can be easily prepared by a two-step process starting with formylation of substituted phenols towards substituted 4-hydroxy-benzaldehyde by using less than one molar equivalent of a formyl carbon source, preferably hexamethylenetetramine, and oxidation of the substituted hydroxy aromatic aldehyde to the corresponding hydroquinone under acidic conditions, preferably provided by sulphuric acid.

The present invention may find application as a commercially attractive method for the preparation of compounds of formula (I). In the meaning of the present invention, the compounds of formula (I), and compounds of any other formulae (II) and (III) hereunder, are defined to include pharmaceutically usable derivatives, solvates, prodrugs, tautomers, enantiomers, racemates and stereoisomers thereof, including mixtures thereof in all ratios. The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent is a prodrug within the scope and spirit of the invention. Various forms of prodrugs are well known in the art and are described (e.g. Wermuth et al., Chapter 31: 671-696, The Practice of Medicinal Chemistry, Academic Press 1996; Bundgaard, Design of Prodrugs, Elsevier 1985; Bundgaard, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centres at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centres of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatisation with an optically active reagent such as, for example, an optically active alcohol, and subsequent elimination of the radical.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the meanings as described below.

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. YY) the expression of such substituent may differ from each other (e.g. methyl and ethyl). It shall be understood accordingly that a multiple substitution of any radical of the invention may involve identical or different radicals. Hence, if individual radicals occur a number of times within a compound, the radicals adopt the meanings indicated, independently of one another.

The terms "alkyl", "alkane" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert.-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, iso-hexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, "A" denotes unbranched or branched alkyl having 1-10 C atoms, in which 1-7 H atoms can be replaced by Hal, and/or in which one or two adjacent $CH_2$ groups can be replaced independently of one another by a —CH═CH— and/or —C≡C— group. A more preferred "A" denotes unbranched or branched alkyl having 1-10 C atoms, in which 1-5 H atoms may be replaced by F, Cl and/or Br. Most preferred is $C_{1-4}$-alkyl. A $C_{1-4}$-alkyl radical is, for example, a methyl, ethyl, propyl, isopropyl, butyl, isobutyl, tert.-butyl, sec-butyl, fluoromethyl, difluoromethyl, trifluoromethyl, pentafluoroethyl, 1,1,1-trifluoroethyl or bromomethyl, especially methyl, ethyl, propyl, isopropyl, butyl or tert.-butyl. It is a highly preferred embodiment of the invention that "A" denotes methyl or ethyl. It shall be understood that the respective denotation of "A" is independently of one another in radicals R2, R3, R5, R6, Y and Cyc.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "Cyc" denotes cycloalkyl having 3-7 C atoms, in which 1-4 H atoms may be replaced independently of one another by A, Hal and/or OY. Moreover, the definition of "A" shall also comprise cycloalkyls and it is to be applied mutatis mutandis to "Cyc".

The term "alkyloxy" or "alkoxy" for the purposes of this invention refers to an alkyl radical according to above definition that is attached to an oxygen atom. The attachment to the compounds of the general formula (I) is via the oxygen atom. Examples are methoxy, ethoxy and n-propyloxy, propoxy, isopropoxy and butoxy. Preferred is "$C_1$-$C_4$-alkyloxy" having the indicated number of carbon atoms.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl(haloalkyl) or alkoxy group (e.g. $CF_3$ and $CF_3O$).

The term "hydroxyl" means an —OH group.

The index n is preferably 0, 1 or 2.

Although the generic formula 0 can even be defined as broad as in EP 0599148 B1 in one embodiment herein, another embodiment of the invention comprises a process for the preparation of compounds of formula (I), wherein
R2, R3, R5, R6 is independently from one another H, A, Hal or OA;
A is unbranched or branched alkyl having 1-10 C atoms, in which 1-5 H atoms can be replaced by Hal; and
Hal is F, Cl or Br.

In a preferred embodiment of the invention, compounds of formula (I) are prepared, wherein
R2 is H or A;
R3, R5 are H, A, Hal or OA;
R6 is H;
A is unbranched or branched alkyl having 1-4 C atoms; and
Hal is F, Cl or Br.

It shall be understood that the compounds of formula (I) are preferably di- or trisubstituted hereunder. In this aspect, the radicals R3 and R5 can be either identical or different, but they are preferably identical.

In a more preferred embodiment of the invention, compounds of formula (I) are prepared, wherein
R2 is H or methyl;
R3, R5 are H, methyl, ethyl, propyl, isopropyl, butyl, tert.-butyl or Hal;
R6 is H; and
Hal is F, Cl or Br.

In a most preferred embodiment of the invention, compounds of formula (I) are prepared, wherein
R2 is H or methyl;
R3, R5 are methyl or ethyl;
R6 is H.

In a highly preferred embodiment of the invention, 2,3,5-trimethylbenzene-1,4-diol and/or 2,6-diethylbenzene-1,4-diol are prepared. It goes without saying that 2,3,5-trimethylbenzene-1,4-diol corresponds to 2,3,5-trimethylhydroquinone (TMHQ). An attractive starting material for TMHQ manufacture according to the invention is 2,3,6-trimethylphenol that is readily available commercially. The intermediate 2,3,5-trimethyl-4-hydroxy-benzaldehyde has never been prepared before the disclosure of this invention. It is synthesised by step (a) of the inventive process and characterised hereunder.

Even though the starting materials are not commercially available, they can be produced by methods known per se, as described in the literature (e.g. in standard works, such as Houben-Weyl, Methoden der organischen Chemie [Methods of Organic Chemistry], Georg-Thieme-Verlag, Stuttgart), i.e. under reaction conditions that are known and suitable for said reactions. If desired, the starting materials can also be formed in-situ by leaving them in the un-isolated status in the crude reaction mixture, but immediately converting them further into the compound according to the invention. On the other hand, it is possible to carry out the reaction stepwise.

The present invention teaches to adjust the reaction conditions of Duff reaction and Dakin reaction in order to obtain the desired high yields of hydroquinone product. In the formylation reaction of step (a), the formyl carbon source is preferably hexamethylenetetramine or a combination of formaldehyde and ammonium acetate. It is more preferred to use hexamethylenetetramine, most preferably 0.01 to 0.49 molar equivalents of hexamethylenetetramine. Highly preferably, 0.3 to 0.4 molar equivalents of hexamethylenetetramine are used without any substantial loss of yield. It shall be understood that "equivalent" denotes the molar ratio of formyl carbon source (e.g. hexamethylenetetramine) to compound of formula (II).

The formylation reaction of the formyl carbon source with the phenol compound of formula (II) is performed in an organic acid, such as a carboxylic acid or sulfonic acid; the suitability of which for formylation can be figured out by the skilled artisan as a matter of routine. A few common examples include lactic acid, acetic acid, formic acid, citric acid, oxalic acid and uric acid. In a preferred aspect of the invention, step (a) of the process is performed in acetic acid. It is more convenient to use glacial acetic acid, particularly in the range of 98 to 100% (v/v), to maximize yield along with minimal impurity formation. Use of recovered acetic acid gives the same yield.

The mixture of phenol compound of formula (II) and formyl carbon source in the organic acid is heated for a period of 1 to 5 hours, preferably 2 to 3.5 hours. The use of an elevated temperature is desirable to obtain homogeneous reaction conditions. Preferably, heating is performed at 80° C. to 135° C., more preferably 90° C. to 135° C. Reflux temperature, particularly at atmospheric pressure, is most convenient and effective and is therefore preferred in a range of 90° C. to 135° C., highly preferably in the range of 110° C. to 130° C.

The heating period in step (a) is followed by quenching a hydrolysis medium in an amount roughly equal to that of the volume of organic acid used (e.g. acetic acid) The hydrolysis medium is preferably water or an aqueous acid, more preferably sulphuric acid, most preferably 10% to 20% (v/v) sulphuric acid. It shall be understood that the skilled artisan knows several other types of aqueous inorganic acids, which are suited in the scope of the present invention, such as HCl, $H_2CO_3$, $H_3PO_4$ and the like. The aqueous mixture is further heated for a short period of time, particularly 0.25 to 1 hour. The heating is performed under the temperature conditions as given above, but highly preferably in a range of 100° C. to 120° C. The reaction of step (a) is stopped by cooling down and the crude intermediate of formula (III) is concentrated, such as by filtration, washing and drying, to yields of at least 60%, preferably at least 70%, more preferably at least 80%, most preferably at least 90%. Alternatively, the reaction solution can be concentrated under vacuum to recover the organic acid, or it is cooled and extracted with a non-polar solvent. Preferred solvents for the extraction are hydrocarbon solvents, such as hexane, heptane, toluene and xylene, or ethers, such as diethyl ether and tert.-butyl methyl ether.

Prior to step (b), the compound of formula (III) can be purified, e.g. by passing the solution in a non-polar solvent, such as hexane or toluene, through a pad of silica gel, and the solvent is stripped from the filtrate to provide a solid. Alternatively, the organic phase can be separated from the aqueous phase, and the organic phase is then re-crystallized in an alcohol solvent, particularly methanol. A preferred downstream-processing is performed by means of an inorganic base, more preferably sodium hydroxide, most preferably 0.1% to 10% sodium hydroxide in a molar ratio of compound of formula (III) to sodium hydroxide from 0.2 to 5. Highly preferably, 1% to 2% sodium hydroxide in an equimolar ratio of compound of formula (III) to sodium hydroxide is applied, in order to enhance purity while the yields are largely kept within the preferred ranges as given above.

In the Dakin oxidation of step (b), the compound of formula (III) is reacted with an oxidising agent, such as ammonium cerium(IV) nitrate, chlorite, chlorate, perchlorate and other analogous halogen compounds, hexavalent chromium compounds (e.g. chromic and dichromic acids and chromium trioxide, pyridinium chlorochromate), chromate/dichromate compounds, hypochlorite and other hypohalite compounds, iodine and other halogens, nitric acid, nitrous oxide, osmium tetroxide, ozone, permanganate salts, peroxide compounds, persulphuric acid, potassium nitrate or sulphoxides. A preferred oxidising agent of the invention is hydrogen peroxide, more preferably 20% to 50% hydrogen peroxide, most preferably 30% hydrogen peroxide, highly preferably approximately 1.2 molar equivalents of 30% hydrogen peroxide.

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Preference is given to water or an organic solvent. It is more preferred to use an alkane or alcohol, more preferably methanol, most preferably 98% to 100% pure methanol.

Furthermore, the reaction is essentially carried out under acidic conditions. It is referred to the organic and inorganic acids already mentioned in the course of prior specification as suitable examples. In step (b), the acidic conditions are preferably provided by sulphuric acid. The amount of used sulphuric acid is more preferably about 0.1 to 0.3 molar equivalents, but best results are obtained by using 0.2 molar equivalents of c.sulphuric acid. In other words, it is more preferred to use sulphuric acid in a molar ratio to the compound of formula (III) from 0.1 to 0.3, most preferably between 0.1 and 0.3, highly preferably sulphuric acid in the molar ratio to the compound of formula (III) of 0.2. The purity of c.sulphuric acid shall particularly amount to at least 98%. It shall be understood that the threshold values are not covered if defining a range "between".

The Dakin reaction is preferably performed at a temperature between 15° C. and 90° C. A temperature range between 15° C. and 50° C. is even more desirable to obtain homogeneous reaction conditions. The temperature may vary during the oxidation that is executed for a period of 0.5 to 2 hours.

After completion of Dakin oxidation, excess hydrogen peroxide and quinone formed by over-oxidation of hydroquinone can be removed. A reducing agent is preferred for reductive removal. Common reducing agents are ferrous ion, lithium aluminium hydride, nascent hydrogen, sodium amalgam, sodium borohydride, sulphite compounds, hydrazine, zinc-mercury amalgam, diisobutylaluminum hydride, oxalic acid or formic acid. It is more preferred to use sodium dithionate, most preferably 10% to 20% sodium dithionate solution in water. The excessive hydrogen peroxide can also be reductively removed by addition of $NaHSO_3$, such as 10% aqueous $NaHSO_3$ in particular. The reductive exposure is at room temperature for 0.5 to 1 hour. Subsequently, the solvent is distilled out in vacuum. Methanol recovery up to 60 to 75% is preferred to improve yield. Solvent distillation is stopped by cooling, and the hydroquinone of formula (I) is concentrated, such as by filtration, washing and drying, to yields of at least 60%, preferably at least 70%, more preferably at least 80%, highly preferably at least 85%. A high purity of more than 97% is particularly obtained for the final hydroquinone product.

A salt of the compounds according to formulae (I) to (III), preferably formula (I), is optionally provided. The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also a compound of formula (III) having sub-formula 2,3,5-trimethyl-4-hydroxy-benzaldehyde. The intermediate is prepared by step (a) of the process according to the invention. On the other hand, the intermediate of the process according to the invention can be used for the preparation of TMHQ. In the practice of the invention, the process allows the production of TMHQ in high yields on an industrial scale. The formylation of 2,3,6-trimethyl-phenol is standardised on 50 kg scale while the oxidation of the intermediate aldehyde is standardised on 20 kg scale. The product is of light colour, stable and of high purity (>97%). The final compound is prepared by the process according to the invention. The prior teaching of the invention and its embodiments is valid and applicable without restrictions to the compound 2,3,5-trimethyl-4-hydroxy-benzaldehyde itself if expedient.

In the scope of the present invention, a promising, novel approach for manufacturing hydroquinones of formula (I) has been provided. The hydroquinone synthesis involves insertion and removal of one carbon atom which is in resemblance with nature and eco-friendly. The process has two steps starting from substituted phenols of formula (II). The use of cheap raw materials is of benefit for an economical process conduct. The key intermediates of substituted hydroxy aromatic aldehydes of formula (III) are advantageously isolated in pure state and characterised by spectral data. Furthermore, the impurities formed in the process are fully characterised by spectroscopic methods and their elimination in the intermediate and final product is well studied. Accordingly, this method has general utility for the conversion of various substituted phenols of formula (II) to substituted hydroquinones of formula (I) via corresponding substituted aldehydes of formula (III). In the practice of the invention the novel process has made it possible to produce TMHQ starting from 2,3,6-trimethylphenol. The final product is of high yields and high purity (>97%).

All the references cited herein are incorporated by reference in the disclosure of the invention hereby.

It is to be understood that this invention is not limited to the particular compounds, uses and processes described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a process" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved.

EXAMPLE 1

Synthesis of 2,6-dichlorobenzene-1,4-diol

A 250 ml three neck round bottom flask fitted with reflux condenser, pot thermometer and mechanical stirrer, was charged with 10 g (0.061 mol) of 2,6-dichlorophenol, 40 ml glacial acetic acid and 3.44 g (0.024 mol) of hexamethylenetetramine. The reaction mass was heated at reflux for 3 hrs (a clear solution was obtained at 70° C.). The progress of reaction was checked by TLC. The mixture was allowed to cool at 100° C.; 30 ml of 10% sulphuric acid were slowly added and stirred at 100° C. for 20-30 min. The reaction mass was poured into 200 g crushed ice. The solid was filtered and washed well with 100 ml water and drying at 70° C. afforded 9.2 g (84%) of 3,5-dichloro-4-hydroxy-benzaldehyde. Melting point: 153-155° C. $^1$H NMR (400 MHz, CD$_3$OD) δ 9.72 (s, 1H), δ 7.80 (s, 1H).

In a 250 ml round bottom flask, a solution of 0.69 g (0.007 mol) of c.sulphuric acid and 40 ml methanol was prepared. 4.5 g (0.023 mol) of 3,5-dichloro-4-hydroxyl-benzaldehyde were added and stirred to obtain a clear solution. The reaction mass was cooled to 17-20° C. and 5.34 g (0.047 mol) of 30% hydrogen peroxide solution were slowly added under stirring (caution: exothermic reaction) over a period of 5-10 minutes under maintaining the temperature at 20-35° C. The mixture was stirred for 30 min at room temperature and at 80° C. for 60 min. The completion of reaction was confirmed by TLC. 15 ml of 20% sodium dithionite solution were slowly added (5-10 min) under stirring at 20-25° C. The mixture was stirred under nitrogen at 20-25° C. for 30 min. 20 ml of aqueous methanol were distilled out at 40-50° C. The reaction mass was cooled to 20-25° C. and 45 ml of process water were added over a period of 5 min. The mixture was stirred for 10-15 min under nitrogen. The product was filtered and washed with 25 ml of process water, suck-dried well and then dried under vacuum at 60° C. for 2 hrs to afford 3.2 g (76%) of 2,6-dichloro-hydroquinone (2,6-dichlorobenzene-1,4-diol). Melting point: 110-112° C.

EXAMPLE 2A

Synthesis of 2,3,5-trimethylbenzene-1,4-diol

A mixture of 2,3,6-trimethylphenol (5 g, 0.036 mol) and hexamethylenetetramine (2.06 g, 0.0147 mol) in acetic acid (20 ml) was stirred at 115° C. for 2 hrs. The solvent (10 ml) was distilled and 20% (v/v) H$_2$SO$_4$ (20 ml) was added, and then the mixture was stirred at 115° C. for 20 min. The mixture was then poured on ice cold water (50 ml) and the separated solid was filtered, washed well with cold water (25 ml) and suck-dried. The wet cake was dried at 90° C. for 2 hrs under vacuum to yield 2,3,5-trimethyl-4-hydroxy-benzaldehyde (4.5 g, 75%; Table 1, no. 12).

A solution of methanol (40 ml) and 0.267 g (0.0027 mol) of sulphuric acid was prepared and stirred. 4-hydroxy-2,3,5-trimethyl-benzaldehyde (4.5 g, 0.027 mol) was added to this solution and stirred to dissolve. 30% hydrogen peroxide (3.46 g, 0.029 mol) was slowly added to this clear solution over 5 minutes. After the completion of addition, the reaction mixture was stirred at room temperature for 30 min. The solvent (20 ml) was evaporated in vacuum and 50 ml of 20% sodium dithionite solution were added under nitrogen atmosphere. The reaction mass was stirred for 30 min at 20-25° C., filtered, washed with cold water, suck-dried well and subsequently dried well at 80° C. under vacuum for 2 hrs to yield 2,3,5-trimethyl-hydroquinone (2,3,5-trimethylbenzene-1,4-diol) as buff coloured solid (3.33 g, 80%; Table 2, no. 13).

EXAMPLE 2B

Synthesis of 2,3,5-trimethylbenzene-1,4-diol

A 500 ml three neck round bottom flask equipped with mechanical stirrer and pot thermometer, was charged with 50 g (0.36 mol) of 2,3,6-trimethyl-phenol, 200 ml glacial acetic acid and 20.61 g (0.14 mol) of hexamethylenetetramine. The reaction mass was refluxed for 2 hrs at 120-130° C. The completion of reaction was confirmed by TLC. 100 ml of acetic acid were distilled out at reflux temperature. The reaction mass was allowed to cool at 100° C. and 50 ml 20% sulphuric acid were slowly added over a period of 5-10 min. The mixture was stirred at 100° C. for 15-30 min. Heating was stopped and the reaction mass cooled to 20° C. in an ice bath. 500 ml process water were added and stirred for 10 min at 20-25° C. The reaction mass was filtered and washed with 300 ml process water. The crude product was dried at 60-80° C. under vacuum to afford 54 g (90%) of crude 2,3,5-trimethyl-4-hydroxy-benzaldehyde. Subsequently, a 1% one equivalent solution of sodium hydroxide was prepared in process water. 54 g of crude 2,3,5-trimethyl-4-hydroxy-benzaldehyde were added to it under stirring at room temperature. The mixture was stirred for 15-20 min and filtered. The residue was to be scraped as impurity. The filtrate was collected, acidified with 19.75 g of glacial acetic acid and filtered. The product was suck-dried under vacuum, dried at 60-80° C. for 3-4 hrs to give 48 g (80%) of pure 2,3,5-trimethyl-4-hydroxy-benzaldehyde as off-white amorphous solid (Table 1, no. 13). Melting point: 135-137° C. $^1$H NMR (400 MHz, CDCl$_3$) δ 10.15 (s, 1H), δ 7.49 (s, 1H), δ 5.32 (bs, 1H), δ 2.58 (s, 3H), δ 2.28 (s, 3H), δ 2.22 (s, 3H).

In a 500 ml round bottom flask, a solution of 5.73 g (0.058 mol) of c.sulphuric acid and 432 ml methanol were prepared. 48 g (0.29 mol) of purified 2,3,5-trimethyl-4-hydroxy-benzaldehyde were added under stirring at room temperature. The mixture was further stirred for 10-15 min to obtain a clear solution. The reaction mass was cooled to 17-20° C. and 38.09 g (0.33 mol) of 30% hydrogen peroxide solution were slowly added under stirring (caution: exothermic reaction) over a period of 20-30 min while maintaining the temperature at 20-35° C. The mixture was stirred for 30 min at room temperature and completion of reaction was confirmed by TLC. 58 ml of 20% sodium dithionite solution were slowly added (15-20 min) under stirring at 20-25° C. The mixture was stirred under nitrogen at 20-25° C. for 30 min. 220 ml of aqueous methanol were distilled out from the reaction mass at 40-50° C. The reaction mass was cooled to 20-25° C. and 480 ml of process water were added over a period of 15-20 min. The mixture was stirred for 10-15 min under nitrogen. The product was filtered and washed with 250 ml of process water, suck-dried well and dried under vacuum at 60° C. for 2 hrs to afford 37.8 g (85%) of 2,3,6-trimethyl-hydroquinone (2,3,5-trimethylbenzene-1,4-diol) as buff coloured solid (Table 2, no. 14). Melting point: 172-174° C.

EXAMPLE 2C

Variable Conditions of Formylation Reaction Under Example 2A and 2B

The formylation of 2,3,6-trimethyl-phenol was initially performed by varying the reaction conditions. Details are listed in Table 1. Nos. 1, 2 and 11 are considered as comparative examples and do not read under the scope of the present invention.

TABLE 1

Conditions of formylation reaction

| No. | Organic base | Hydrolysis medium | Molar ratio C$_6$H$_{12}$N$_4$ to 2,3,6-TMP | Temp. [° C.] | Time [hrs] | Yield | Colour of product |
|---|---|---|---|---|---|---|---|
| 1 | AcOH | 1:1 HCl | 1.0 eq | 100 | 3 | 75% | orange |
| 2 | AcOH | cold water | 1.0 eq | 105 | 2 | 74% | orange |
| 3 | AcOH | cold water | 0.2 eq | 105 | 3 | — | — |
| 4 | AcOH | cold water | 0.4 eq | 105 | 3 | 60% | orange |
| 5 | 75% AcOH | cold water | 0.4 eq | 105 | 3 | 60% | off-white |
| 6 | AcOH | 1:1 HCl | 0.5 eq | 105 | 3 | 66% | off-white |
| 7 | 75% AcOH | cold water | 0.5 eq | 105 | 3 | 66% | off-white |
| 8 | AcOH | cold water | 0.6 eq | 104 | 3 | 63% | orange |
| 9 | 80% AcOH | cold water | 0.6 eq | 104 | 3.5 | 64% | off-white |
| 10 | AcOH | cold water | 0.5 eq | 105 | 3 | 71% | orange |
| 11 | AcOH | cold water | 1.2 eq | 105 | 3 | 65% | orange |
| 12 | AcOH | 20% H$_2$SO$_4$ | 0.4 eq | 115$_{reflux}$ | 2 | 75% | buff |
| 13 | AcOH | 20% H$_2$SO$_4$ | 0.4 eq | 120-130$_{reflux}$ | 2 | 90% | buff | eq—equivalent
AcOH—acetic acid

EXAMPLE 2D

Formylation of 2,3,6-Trimethyl-Phenol with Formaldehyde and Ammonium Acetate

Instead of hexamethylenetetramine as applied in Example 2A and 2B, formaldehyde and ammonium acetate in acetic acid were used for formylation as illustrated below. A 250 ml three neck round bottom flask equipped with a reflux condenser was charged with 20.4 g (0.15 mol) of 2,3,6-trimethylphenol. 100 ml acetic acid, 3.09 g (0.04 mol) of ammonium acetate and 3.243 g (0.04 mol) of formalin solution were added to it. The reaction mass was heated at 120° C. over a period of 2.5 hrs. The completion of reaction was confirmed by TLC. The reaction mass was poured into 400 ml ice cold water with stirring. The solid was filtered and washed with 2×50 ml process water. The product was dried under vacuum to afford 17 g (75%) of crude 2,3,5-trimethyl-4-hydroxybenzaldehyde. The purification of crude product with 1% sodium hydroxide solution afforded 13 g (53%) of pure 2,3,5-trimethyl-4-hydroxyl-benzaldehyde.

EXAMPLE 2E

Variable Conditions of Dakin Oxidation Under Example 2A and 2B

The Dakin reaction of 2,3,5-trimethyl-4-hydroxy-benzaldehyde was initially performed by varying the reaction conditions. Details are listed in Table 2. Nos. 1 to 12 are considered as comparative examples and do not read under the scope of the present invention.

TABLE 2

Conditions of Dakin oxidation

| No. | Solvent | Base/acid | Oxidising agent | Yield | Colour of product |
|---|---|---|---|---|---|
| 1 | water | 1 eq NaOH | 30% $H_2O_2$ | 20% | brown |
| 2 | water | 1 eq NaOH | 10% $H_2O_2$ | 62% | brown |
| 3 | water | 2 eq NaOH | 10% $H_2O_2$ | 50% | gray |
| 4 | water | 1 eq NaOH | 3% $H_2O_2$ | 40% | brown |
| 5 | water | 1 eq NaOH | 5% $H_2O_2$ | 55% | buff |
| 6 | hexane | 1 eq NaOH | 3% $H_2O_2$ | 30% | brown |
| 7 | DCM | 1 eq NaOH | 30% $H_2O_2$ | 30% | orange |
| 8 | hexane | 1 eq $Na_2CO_3$ | 30% $H_2O_2$ | 40% | brown |
| 9 | water | 1 eq $Na_2CO_3$ | 30% $H_2O_2$ | 70% | brown |
| 10 | water | 0.5 eq NaOH 0.5 eq $Na_2CO_3$ | 30% $H_2O_2$ | 60% | brown |
| 11 | water | 1 eq NaOH 0.5 eq $Na_2CO_3$ | 30% $H_2O_2$ | 40% | brown |
| 12 | DCM | $Na_2CO_3$ | UHP | 20% | brown |
| 13 | methanol | 0.1 eq c.$H_2SO_4$ | 30% $H_2O_2$ | 80% | off-white |
| 14 | methanol | 0.2 eq c.$H_2SO_4$ | 30% $H_2O_2$ | 85% | off-white |
| 15 | methanol | 0.3 eq c.$H_2SO_4$ | 30% $H_2O_2$ | 80% | off-white | eq—equivalent;
DCM—dichloromethane

EXAMPLE 3

Synthesis of Further Substituted Hydroquinones of Formula (I)

The methodology of this invention has been extended for the manufacture of other antioxidants presently used. In accordance with Example 2B, the compounds of Table 3, nos. 3 & 4, were prepared by employing a molar ratio of substituted phenol to hexamethylenetetramine of 1:0.4, and glacial acetic acid (550 ml of organic base per mol of substituted phenol). The reflux time was 2-3 hrs.

TABLE 3

Summary of compound characteristics of Examples 1 to 4

| No. | R3, R5 (R3 = R5) | R2 | R6 | Yield [%] aldehyde of formula (III) | Melting point [° C.] | Yield [%] hydroquinone of formula (I) | Melting point [° C.] |
|---|---|---|---|---|---|---|---|
| 1 | Cl | H | H | 84 | 153-155 | 76 | 110-112 |
| 2B | methyl | methyl | H | 80 | 135-137 | 80 | 172-174 |
| 3 | isopropyl | H | H | 85 | 100-102 | 80 | 96-98 |
| 4 | ethyl | H | H | 80 | 92-94 | 85 | 94-96 |

The invention claimed is:

1. A process for the preparation of 2,3,5-trimethylbenzene-1,4-diol, comprising the steps of:
   (a) heating to reflux temperature 2,3,6-trimethyl-phenol with 0.3 to 0.4 equivalents of hexamethylenetetramine in an organic acid, followed by adding a hydrolysis medium, which is an aqueous acid, and heating the resulting mixture to yield 2,3,5-trimethyl-4-hydroxy-benzaldehyde, and
   (b) reacting 2,3,5-trimethyl-4-hydroxy-benzaldehyde with an oxidizing agent in a solvent under acidic conditions to yield 2,3,5-trimethylbenzene-1,4-diol.

2. The process according to claim 1, wherein in step (a) the organic acid is glacial acetic acid.

3. The process according to claim 1, wherein in step (a) the heating is performed at reflux temperature of 90° C. to 135° C., or in step (b) the reaction is performed at a temperature between 15° C. and 50° C.

4. The process according to claim 1, wherein in step (b) the oxidizing agent is hydrogen peroxide, or the solvent is an alcohol.

5. The process according to claim 1, wherein in step (b) the acidic conditions are provided by sulfuric acid in a molar ratio to 2,3,5-trimethyl-4-hydroxy-benzaldehyde from 0.1 to 0.3.

6. The process according to claim 1, wherein prior to step (b), 2,3,5-trimethyl-4-hydroxy-benzaldehyde is purified with sodium hydroxide in a molar ratio of 2,3,5-trimethyl-4-hydroxy-benzaldehyde to sodium hydroxide from 0.2 to 5.

7. The process according to claim 1, wherein after step (b), 2,3,5-trimethylbenzene-1,4-diol is purified with a reducing agent.

8. The process according to claim 1, wherein said hydrolysis medium is sulfuric acid.

9. The process according to claim 3, wherein said reflux temperature is in the range of 110° C. to 130° C.

10. The process according to claim 5, wherein said molar ratio is 0.2.

11. A process for the preparation of 2,6-diethylbenzene-1,4-diol, comprising the steps of:
   (a) heating to reflux temperature 2,6-diethyl-phenol with 0.3 to 0.4 equivalents of hexamethylenetetramine in an organic acid, followed by adding a hydrolysis medium, which is an aqueous acid, and heating the resulting mixture to yield 3,5-diethyl-4-hydroxy-benzaldehyde, and
   (b) reacting 3,5-diethyl-4-hydroxy-benzaldehyde with an oxidizing agent in a solvent under acidic conditions to yield 2,6-diethylbenzene-1,4-diol.

12. The process according to claim 11, wherein in step (a) the organic acid is glacial acetic acid.

13. The process according to claim 11, wherein in step (a) the heating is performed at reflux temperature of 90° C. to 135° C., or in step (b) the reaction is performed at a temperature between 15° C. and 50° C.

14. The process according to claim 11, wherein in step (b) the oxidizing agent is hydrogen peroxide, or the solvent is an alcohol.

15. The process according to claim 11, wherein in step (b) the acidic conditions are provided by sulfuric acid in a molar ratio to 3,5-diethyl-4-hydroxy-benzaldehyde from 0.1 to 0.3.

16. The process according to claim 11, wherein prior to step (b), 3,5-diethyl-4-hydroxy-benzaldehyde is purified with sodium hydroxide in a molar ratio of 3,5-diethyl-4-hydroxy-benzaldehyde to sodium hydroxide from 0.2 to 5.

17. The process according to claim 11, wherein after step (b), 2,6-diethylbenzene-1,4-diol is purified with a reducing agent.

18. The process according to claim 11, wherein said hydrolysis medium is sulfuric acid.

19. The process according to claim 13, wherein said reflux temperature is in the range of 110° C. to 130° C.

20. The process according to claim 15, wherein said molar ratio is 0.2.

\* \* \* \* \*